United States Patent
Bucciaglia et al.

(10) Patent No.: US 8,366,086 B2
(45) Date of Patent: Feb. 5, 2013

(54) FRANGIBLE OPENER

(75) Inventors: Joseph D. Bucciaglia, Louisville, CO (US); Victor D. Dolecek, Englewood, CO (US); Darryl Hudock, Highlands Ranch, CO (US)

(73) Assignee: Terumo BCT, Inc., Lakewood, CO (US)

( * ) Notice: Subject to any disclaimer, the term of this patent is extended or adjusted under 35 U.S.C. 154(b) by 514 days.

(21) Appl. No.: 12/625,095

(22) Filed: Nov. 24, 2009

(65) Prior Publication Data

US 2010/0132512 A1    Jun. 3, 2010

Related U.S. Application Data

(60) Provisional application No. 61/119,592, filed on Dec. 3, 2008.

(51) Int. Cl.
- *B23Q 3/08*    (2006.01)
- *B67B 7/00*    (2006.01)
- *B67B 7/14*    (2006.01)
- *B67B 7/18*    (2006.01)
- *B26B 15/00*   (2006.01)

(52) U.S. Cl. .................... 269/32; 81/3.2; 81/3.4; 30/264
(58) Field of Classification Search ................. 269/3, 32
See application file for complete search history.

(56) References Cited

U.S. PATENT DOCUMENTS

| | | | |
|---|---|---|---|
| 1,599,738 A * | 9/1926 | Atkins | 29/261 |
| 4,770,401 A * | 9/1988 | Donaldson | 269/249 |
| 4,878,705 A * | 11/1989 | Arnquist | 294/116 |
| 4,973,328 A | 11/1990 | Smith | |
| 5,446,388 A * | 8/1995 | Chick | 324/550 |
| 6,527,405 B2 * | 3/2003 | Hsieh | 362/119 |
| 7,406,769 B1 * | 8/2008 | Toussaint | 30/93 |
| 2009/0235537 A1 * | 9/2009 | Fisher | 30/264 |

FOREIGN PATENT DOCUMENTS

| DE | 9306976 U1 | 9/1993 |
|---|---|---|
| WO | 93/17734 A1 | 9/1993 |

OTHER PUBLICATIONS

PCT/US2009/065710, "International Search Report," mailed Mar. 15, 2010, (3 pages).
PCT/US2009/065710, "Written Opinion," mailed Jun. 16, 2011, (6 pages).
Frangible opener of unknown origin; color front and side views, photographed Aug. 11, 2008, 2 pages.
Frangible opener of unknown origin; black and white front and side views, photographed Aug. 11, 2008, 2 pages.

* cited by examiner

*Primary Examiner* — Monica Carter
*Assistant Examiner* — Seahee Yoon
(74) *Attorney, Agent, or Firm* — René A. Pereyra

(57) ABSTRACT

A hand held opener for opening a frangible closer comprising a handle adapted to be gripped by an operator, a motion actuator operatively connected to the handle, a first shaft connected to the motion actuator, a second shaft connected to the motion actuator, a first gripper portion on the first shaft adapted to grip the frangible closer in a first location, and a second gripper portion on the second shaft adapted to grip the frangible closer in a second location wherein the motion actuator provides reciprocal movement to the shafts to rotate the frangible closer in one direction and to rotate the frangible closer in a direction opposite the first direction.

11 Claims, 10 Drawing Sheets

FRANGIBLE OPENER

CROSS-REFERENCE TO RELATED APPLICATIONS

This application claims the benefit of U.S. Provisional Application No. 61/119,592, filed Dec. 3, 2008.

FIELD OF THE INVENTION

The instant invention relates to a hand held opener to open frangible closers or stoppers including such closers or stoppers for medical tubing.

BACKGROUND

Frangible closers are closers, pins or stoppers primarily inside tubing or conduits, or inside bag or container ports, to block fluid flow through such tubing or port. Such closers can be broken which opens the tubing or port to permit fluid flow there through. The opening of such stoppers or closers is achieved by external manipulation of the tubing conduit or port without penetration of the sterile or closed condition of the system containing the tubing or port. Such closers or stoppers are manipulated from outside the tubing or port by an external force typically produced by an operator or user of the tubing or system. This force breaks the frangible pin or closer or stopper portion to permit fluid flow through the tubing or port. The force needs to bend or move the frangible closer in two opposite directions to achieve the pin, closer, or stopper breakage.

Generally, frangible closers are manually manipulated to open the tubing or port as described above. Such manipulation requires the operator to grasp the frangible area with both hands and then to twist, bend or rotate such area in one direction followed by a twist, bend or rotation in the opposite direction. This movement is required because a typical frangible closer needs to be broken in two opposed locations. This motion is generally achieved by wrist rotation and may need to be repeated on each side for a complete break of the internal pin, stopper or closer. Complicated multiple disposable or tubing lines may require an operator to open a number of frangible openers or stoppers which may result in wrist or hand strain or a repetitive motion injury.

A need exists for a frangible opener, which can be used with apparatus that uses medical tubing or disposable sets. Such apparatus can be a blood component separation centrifuge that utilizes a closed system disposable including blood tubing and frangibles during the process of separating a biological fluid such as blood into components.

SUMMARY

One object of the instant invention is to provide a hand held frangible opener that avoids repetitive strain injuries on the part of the user.

An additional object of the instant invention is to provide a hand held frangible opener that can be easily transported to apparatus utilizing medical tubing with frangible closers or stoppers.

One embodiment of the instant invention relates to a hand held frangible opener having a handle adapted to be gripped by an operator, a motion actuator, a first shaft connected to the motion actuator, a second shaft connected to the motion actuator, a first gripper portion on the first shaft adapted to grip the frangible closer in a first location, and a second gripper portion on the second shaft adapted to grip the frangible closer in a second location wherein the motion actuator provides movement to the shafts to bend the frangible closer in one direction and to bend the frangible closer in a direction opposite the first direction.

Another embodiment of the instant invention includes a method of opening a frangible opener located in tubing using a hand held frangible opener having first and second shafts operatively connected to a motion actuator comprising, gripping by an operator a handle on the hand held frangible opener, positioning the hand held frangible opener such that one side of the frangible closer fits between a gripper end of the first shaft and the opposite end of the frangible opener fits between a gripper end of the second shaft, powering the motion actuator, moving the first shaft in one direction and moving the second shaft in a direction opposite the first direction.

BRIEF DESCRIPTION

DESCRIPTION

A frangible closer or stopper may include a flexible housing formed of polyvinylchloride polymer or other polymer with a rigid element, closer or stopper portion or pin contained therein. The housing may be inserted between lines or conduits of flexible medical tubing by solvent bonding or other well-known methods. The rigid element, closer or stopper portion or pin prevents fluid flow through the tubing or conduits. Such a frangible closer is shown at 23, 33 and 43 in FIG. 1 at 23, in FIG. 2 and at 23 in FIGS. 3 through 5, and FIGS. 8 through 16.

A frangible closer may also be a rigid element, or closer or stopper portion or pin inserted into, rather than solvent bonded to, tubing or conduits. A frangible closer can also be included in a rigid port structure rather than the tubing.

It is further understood, that a frangible closer or stopper can be any element that blocks tubing, lines, conduit or ports until such element is manipulated to break and permit fluid flow there through, and wherein such manipulation can be done without breaking or opening the tubing, line, conduit or port itself to the atmosphere.

The terms frangible, frangible stopper or frangible closer are used synonymously throughout this description.

Figure 1:
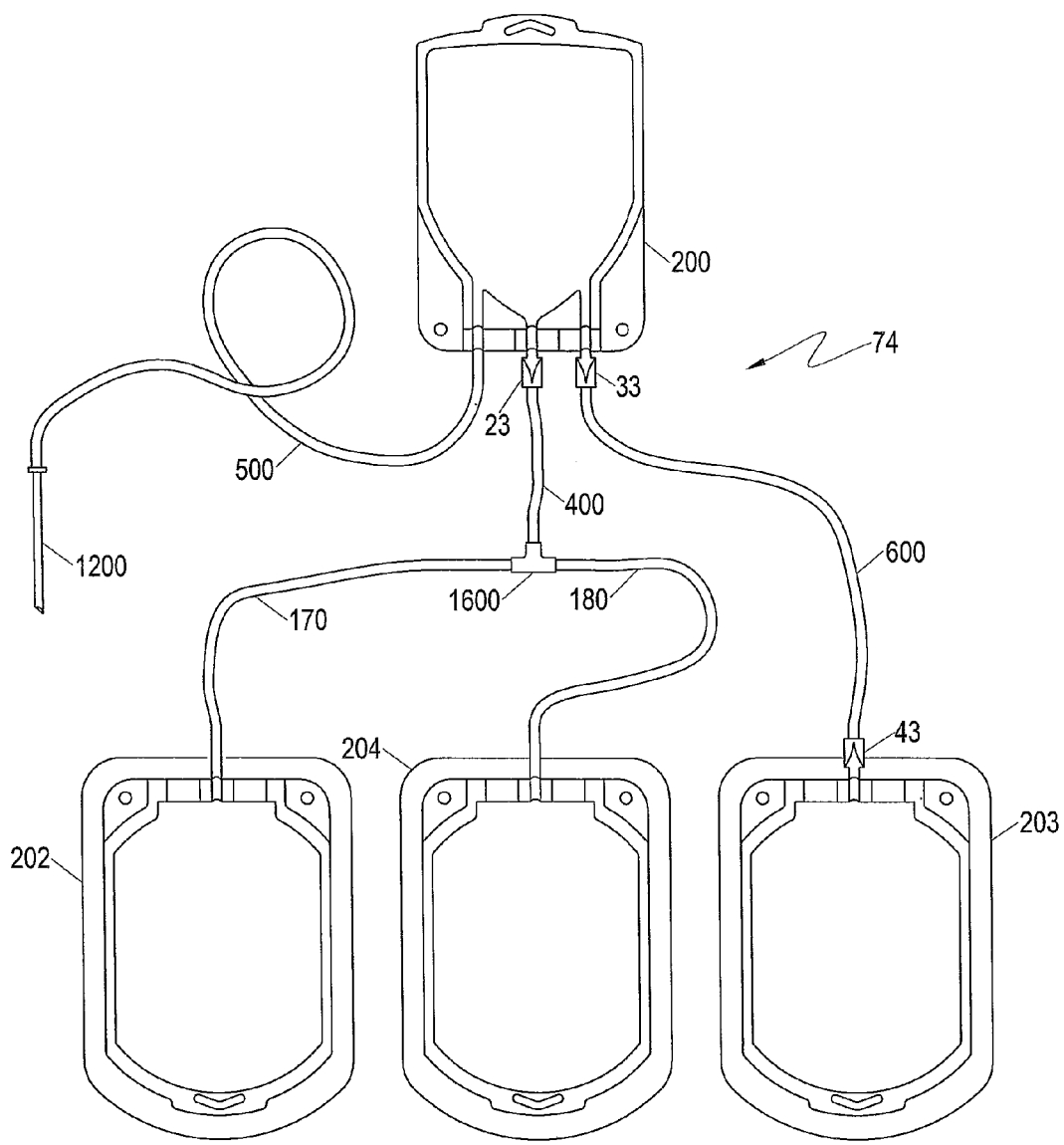
FIG. 1 is a schematic view of a representative disposable bag set for a centrifuge, wherein the bag set includes several frangible closers or stoppers.

FIG. 1 illustrates a bag set 74 for blood separation that includes several frangible closers or stoppers. The bag set may include a whole blood collection or processing bag or container 200, connected to tubing or conduit 500, which is also connected to spike 1200 for anticoagulant or other fluids. Processing bag 200 may also be connected through frangible 23 to tubing or conduit 400 and through connector 1600 to conduit or tubing 170 and product bag or container 202. Processing bag 200 further may be connected through connector 1600 through conduit 180 to alternate product bag or container 204. Frangible 23, before breakage and when closed, prevents collected blood product from leaving collection or processing bag 200 before processing.

Processing bag 200 may also be connected through frangible 33 to conduit or tubing 600, and through conduit or tubing 600 to bag or container 203, which may contain storage solution for a separated component. Frangible 43 may also be provided in conduit or tubing 600. Frangible 33, before breakage and when closed assures that collected blood remains in processing or collection bag 200 before processing. Frangible 43, before breakage and when closed, assures that any component storage solution remains in bag 203 until needed. After processing of the whole blood or the material to be processed in bag 200, such storage solution can flow through conduit 600 to mix with any remaining components in bag 200 or through bag 200 to component bags 202 or 204.

Figure 5:
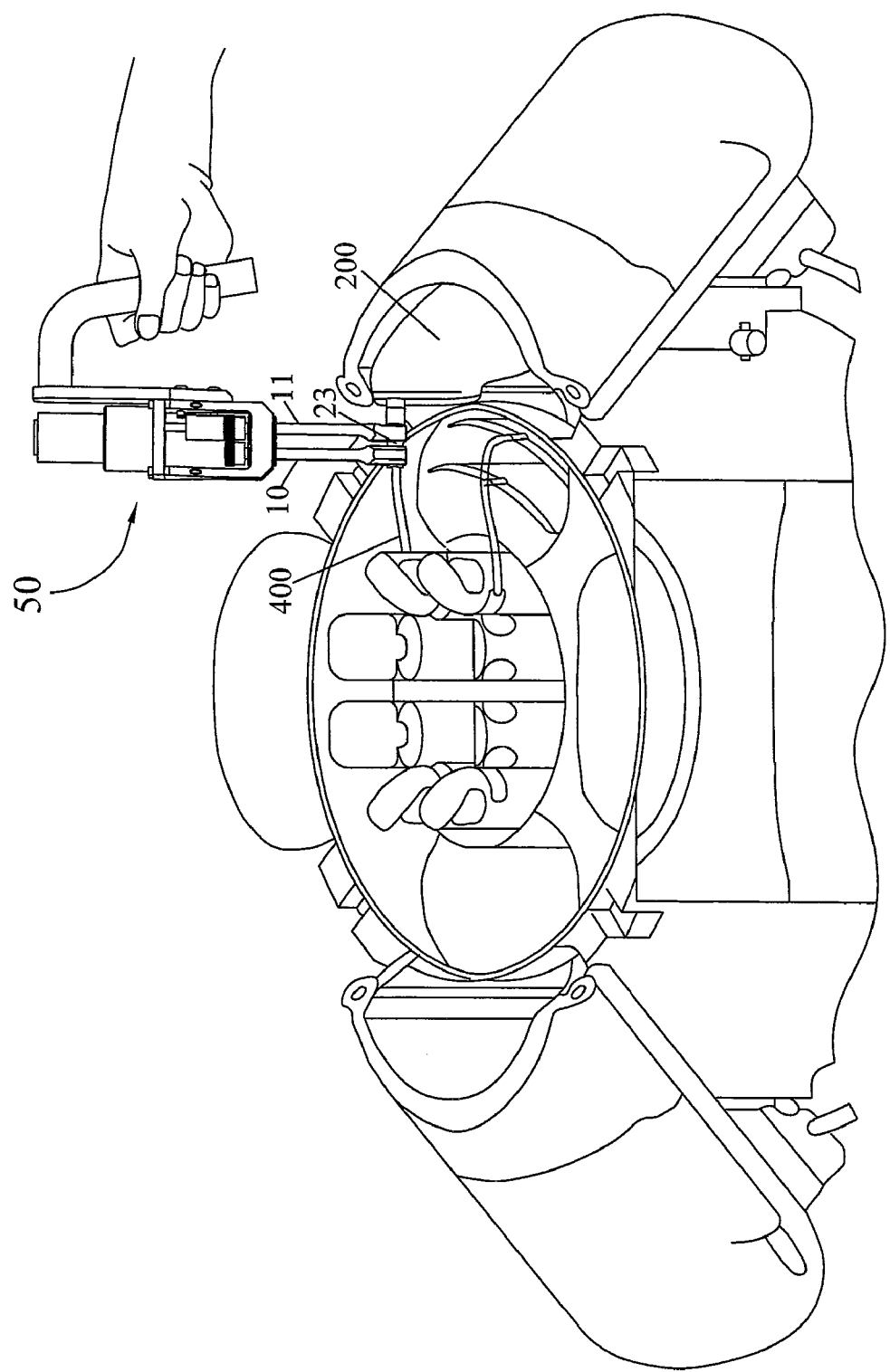
FIG. 5 is a perspective view of apparatus for receiving a bag set and an operator with the frangible opener.

A bag set such as that shown in FIG. 1 may be utilized in a centrifuge apparatus such as that shown in FIG. 5 for the separation of blood into components. Such apparatus is described in PCT Publication WO2007/001739 and PCT Publication WO2007/001754.

The bag set of FIG. 1 is only one example of a bag or disposable set utilizing frangible closures. It is only a representative bag set in that the frangible opener of the instant invention may be utilized to open frangibles in any tubing, conduit or port or similar structure.

Figure 2A:
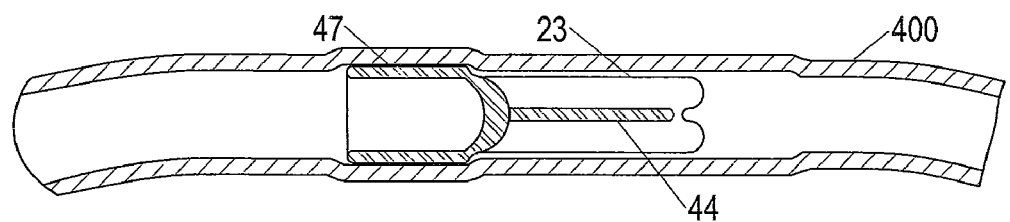
FIG. 2a is a perspective view in cross section of a typical frangible closer in a closed configuration.
Figure 2B:
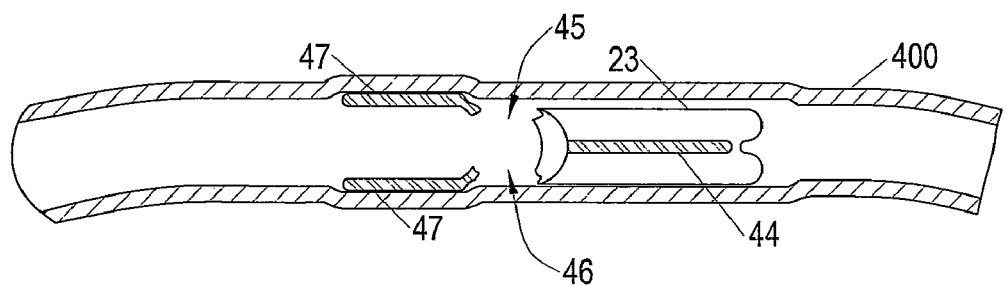
FIG. 2b is a perspective view in cross section of a typical frangible closer in an open configuration.

FIGS. 2a and 2b illustrates a typical frangible closer such as 23 shown in a conduit such as 400. FIGS. 2a and 2b are enlarged to better show the frangible closer 23. Such frangible closer 23 includes U shaped portion 43 and stem or action portion 44. Manipulation of stem or action portion 44 through representative conduit 400, with such manipulation being in opposite directions causes U-shaped portion 47 to bend and break at the junctions where the U is formed to provide fluid passages 45 and 46.

Figure 3:
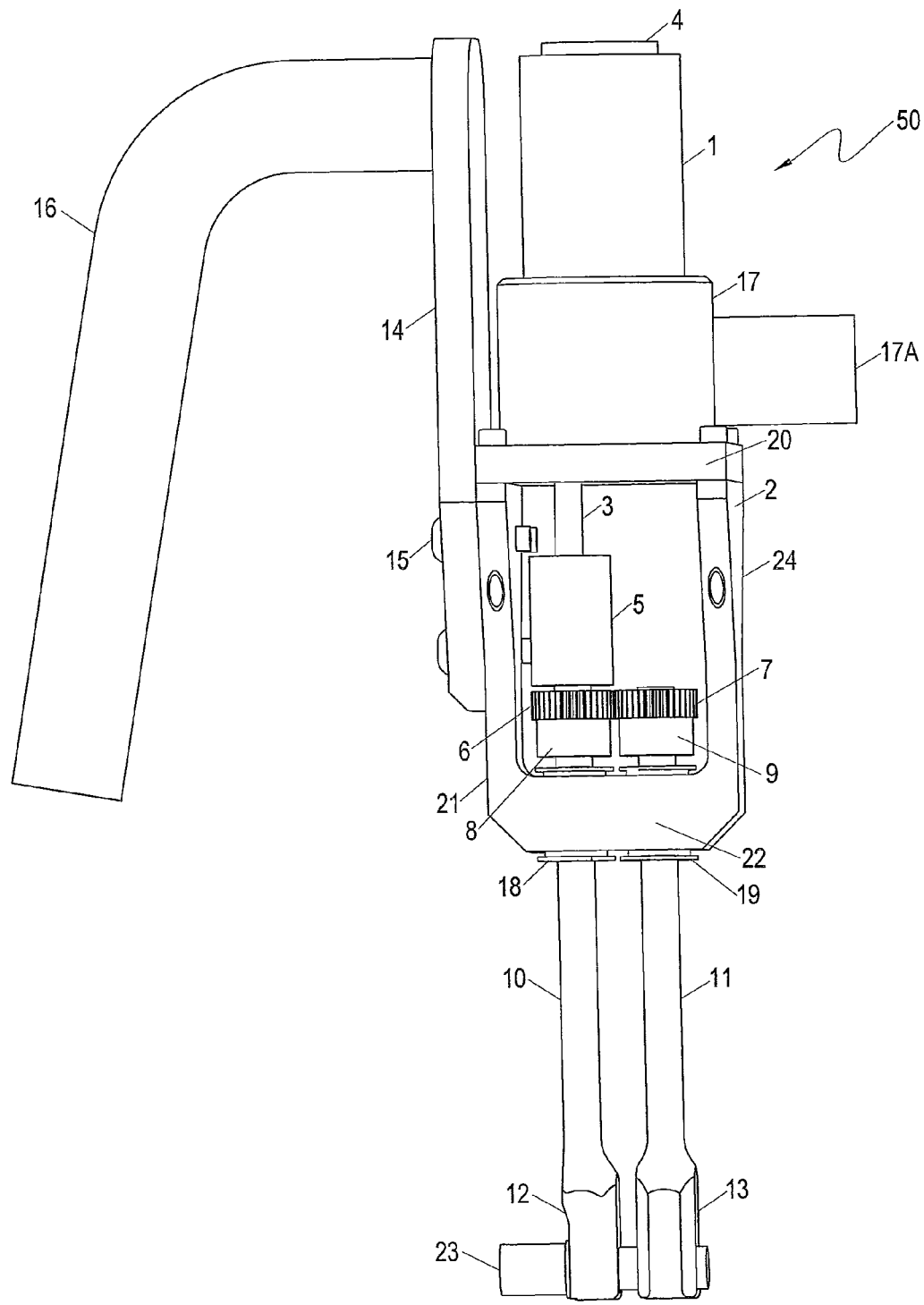
FIG. 3 is a side perspective view of a hand held frangible opener before opening a frangible closer.
Figure 4:
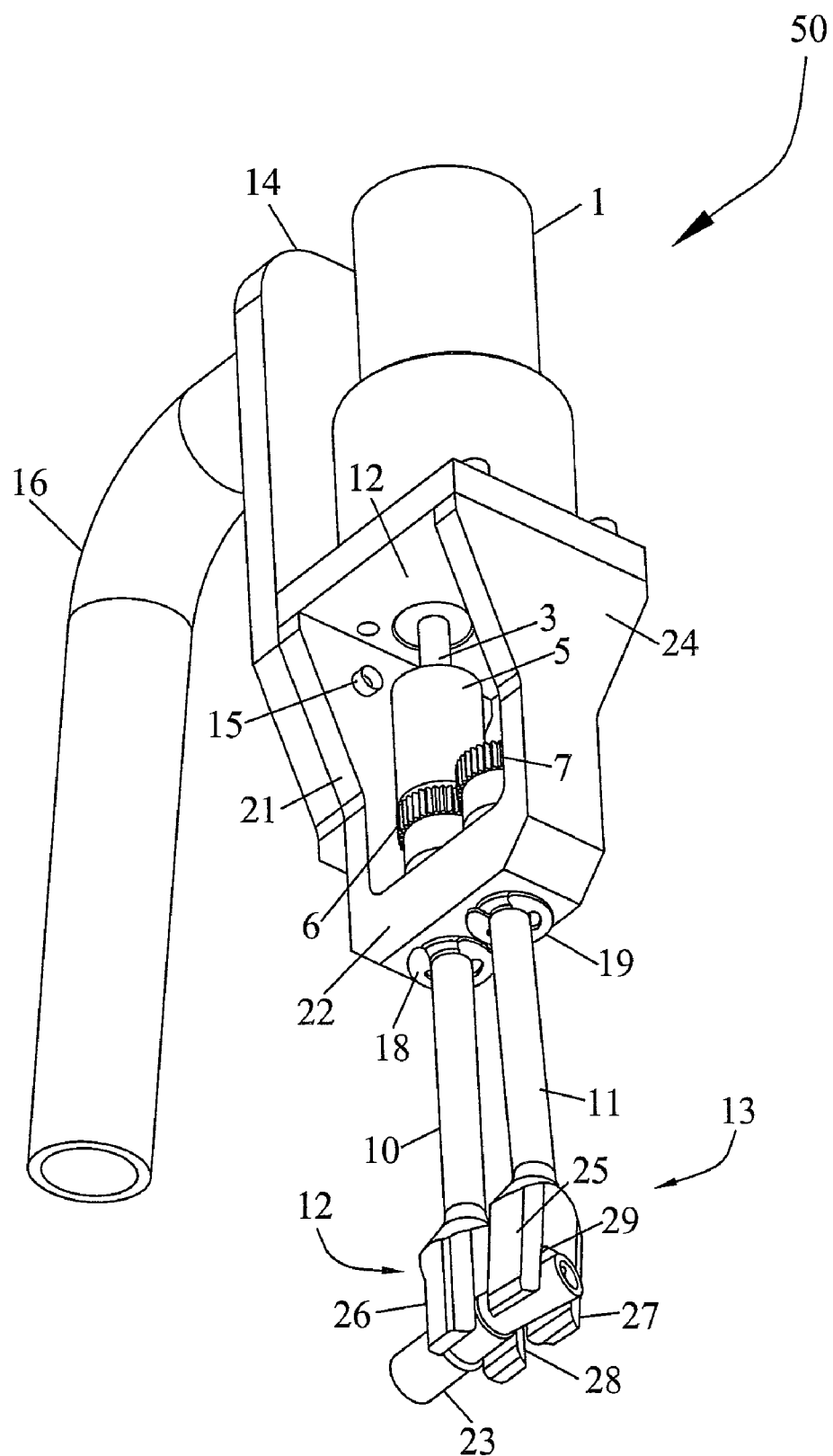
FIG. 4 is also a side perspective view of the hand held frangible opener after opening the frangible closer.

FIGS. 3 and 4 illustrate one embodiment of the frangible opener 50 of the instant invention utilized with frangible 23 for description purposes. It is understood that frangible 23 is included inside tubing, not shown. It is further understood the opener can be used to similarly open frangible closers or stoppers 33 and 43.

Frangible opener 50 is to be held and operated by an operator or user of the disposable bag set 74 and its associated apparatus. Opener 50 includes an optional handle 16, which may be curved to best accommodate the operator's hand. The handle 16 is attached to the opener 50 by bracket 14 and attachment devices such as screws, staples or nails 15. Any number of attachment devices can be used to assure secure contact between the handle and the other parts of the opener 50. It is also contemplated that handle 16 can optionally be pivoted or rotated about attachment devices 15 to best position the handle 16 in order to reach less accessible frangible closers. The operator may also use housing portion 1 as the handle as handle 16 is optional.

Attachment devices 15, which may vary in number, attach the handle 16 to harness 2. The harness 2 includes crosswise upper portion 20 that may be in contact through adhesive or other known attachment devices to motor 17. Harness 2 further includes two side portions 21 and 24, one of which is connected to bracket 14 through attachment devices 15. Harness 2 further includes bottom portion 22, which contains apertures for shafts 10 and 11 as described below.

Motor or electric power system 17 drives a gear assembly as described below. The motor 17 may be included in a motor housing if desirable. In such a case, 17 would depict the housing. The motor 17 is also electrically attached to batteries or another electrical power system housed in housing 1. Such batteries or system power the motor 17 and are electrically connected to switch 4 for on/off operation of the motor.

Any batteries may optionally be of the rechargeable type and housing 1 may fit in a recharging station (not shown) for the batteries contained therein.

As is readily apparent the frangible opener 50 can also be powered by external electricity connected through a switch, such as 4, to motor 17. It is also understood that the switch 4 may be located on the handle 16 if desired with a suitable known electrical connection to batteries in housing 1 or the external electrical source.

The frangible opener 50 may also optionally include a light 17A mounted on motor 17 and electrically connected to batteries in 1 and switch 4 to illuminate any frangible to be opened.

Motor 17 is connected through motor shaft 3 with enlarged section or crank 5 of first and second gear arrangements 6 and 7. These gear arrangements 6 and 7 are keyed or toothed such that rotation of gear 6 counterclockwise causes rotation of the other gear 7 clockwise. Similarly, when gear 6 rotates clockwise gear 7 rotates counterclockwise.

Gear arrangement 6 is connected to first opener shaft 10 by hub 8. This geared shaft 10 passes through bottom portion 22 of harness 2 and through washer connection 18. Similarly, gear arrangement 7 is connected to second gear or opener shaft 11 by hub 9, which also passes through bottom portion 22 of harness 2 and through second washer connector 19. Shaft 10 terminates in first gripper end 12 while shaft 11 terminates in second gripper end 13.

Gripper end 12 includes one side element 26 and opposing side element 28 (see FIG. 4). These side elements are arranged in size so that a frangible, such as 23, can fit between the side elements to rest against a base portion (not shown for gripper end 12, 29 for gripper end 13) of the gripper ends 12, 13.

Similarly, gripper end 13 includes side elements 25 and 27 with base portion 29 there between.

The frangible opener 50 may be made from a variety of materials such as rigid plastic or polymer materials or various metals. Alternatively, a plurality of materials may be used for the frangible opener with some portions, such as the handle, being of plastic material, with other portions being metal. One constraint on the materials used is that such materials be light enough for the operator to hold and that the gearing, shafts and gripper be strong enough to break the frangible pin or element contained within the frangible 23.

Cushion elements may also be used on the frangible opener 50 if desirable. Such cushion elements or padding may be used on the handle 16 and the switch 4. If no handle is provided and the operator grips housing 1, such cushion elements may also be provided on housing 1.

Similarly, a tacky coating or material may be used to enhance cooperation between the frangible opener and the operator through use of such coating on handle 16, housing 1 or switch 4. Similarly tacky coating or material may be used between the gripper ends 25, 26, 27 and 28 and the (not shown) tubing to enhance cooperation. Such tacky coating or material could also be applied to base elements such as 29.

The gearing 6, 7 and the motor 17 are such that when the motor rotates one direction, such as clockwise, gear 6 and associated shaft 10 will also rotate clockwise. However, gear 7 and associated shaft 11 will rotate counterclockwise. This movement bends the frangible opener in one direction. Thus, when gripper ends 26 and 25 move opposite each other, gripper ends 27 and 28 will move toward each other. Similarly when gripper ends 26 and 25 move toward each other the movement of 27 and 28 will be opposite each other and the frangible opener will bend in the opposite direction. This movement effectively snaps or breaks the frangible rigid U-shaped element or portion 43. The motor can stop after rotation in one direction with the movement being reversed on the next switch contact or the motor can produce reciprocating motion of the shafts 10, 11 for each actuation. A limit switch or other sensor can be used to indicate the end of rotation in either direction. This can be used to trigger rotation in the opposite direction.

FIG. 5 illustrates the frangible opener in use with the disposable or bag set of FIG. 1. As shown, the frangible opener 50 can be used to open frangible 23 (inside conduit) in line 400 connected to bag 200. The frangible opener 50 can also be used to open the frangibles 33 and 43 by reaching the frangibles with the frangible opener. In operation, and as a result of the gearing, the gear shafts 10 and 11 will each move in its first rotational direction to bend the frangible opener one direction and to snap or break one side of the U-shaped portion 43 inside the tubing 400. The gearing will then cause each gear shaft 10 and 11 to move in a direction opposite from its first rotational direction to bend the frangible opener an opposite direction and to snap the other side of the U-shaped portion 43 to completely break the pin or stopper. The procedure can be repeated if needed. A similar process occurs with the alternative embodiments of FIGS. 6-12. In each of these embodiments, only the frangible 23 closer is shown for illustration purpose. It is in understood that the frangible closer will be inside tubing or conduit, such as 400.

An alternate frangible opener 150 is shown in FIGS. 6-9. This embodiment includes a streamlined outer casing 116, which forms a handle for the user or operator. Extending from the casing is opener shaft 110 having gripper end 112 and opener shaft 111 having gripper end 113. The gripper ends can be similar to those described with respect to the embodiment of FIGS. 3 and 4. Each opener shaft 110 and 111 may optionally have cutout portion 115 (not shown for opener shaft 111) to minimize the weight of the overall opener 150.

Figure 6:
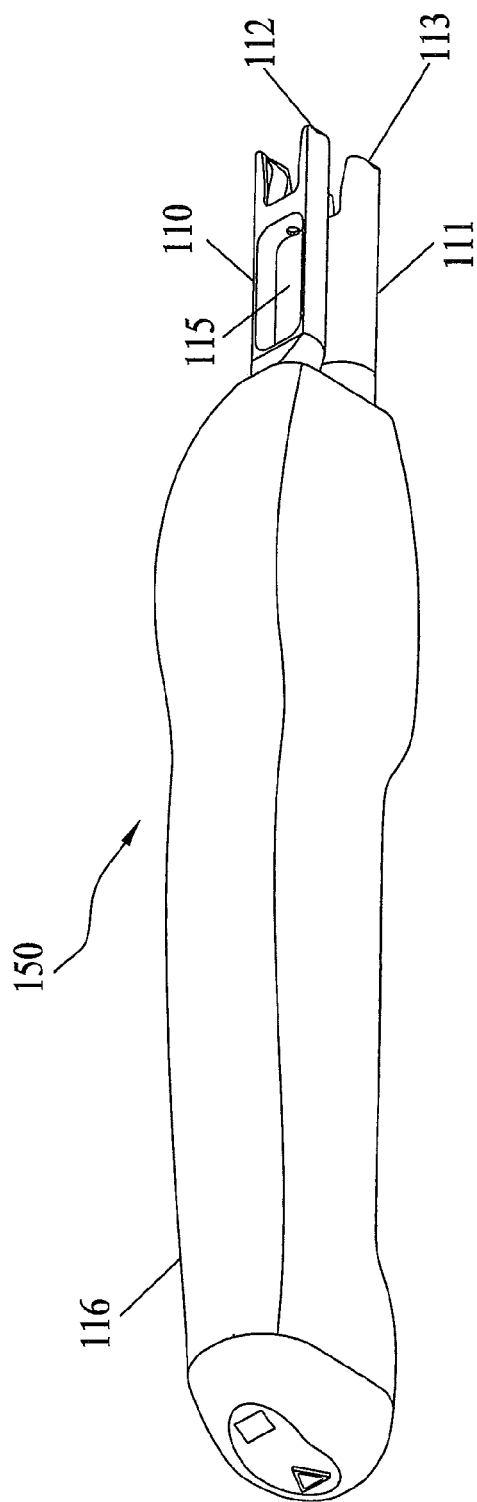
FIG. 6 is a perspective view of an alternative frangible opener.
Figure 7:
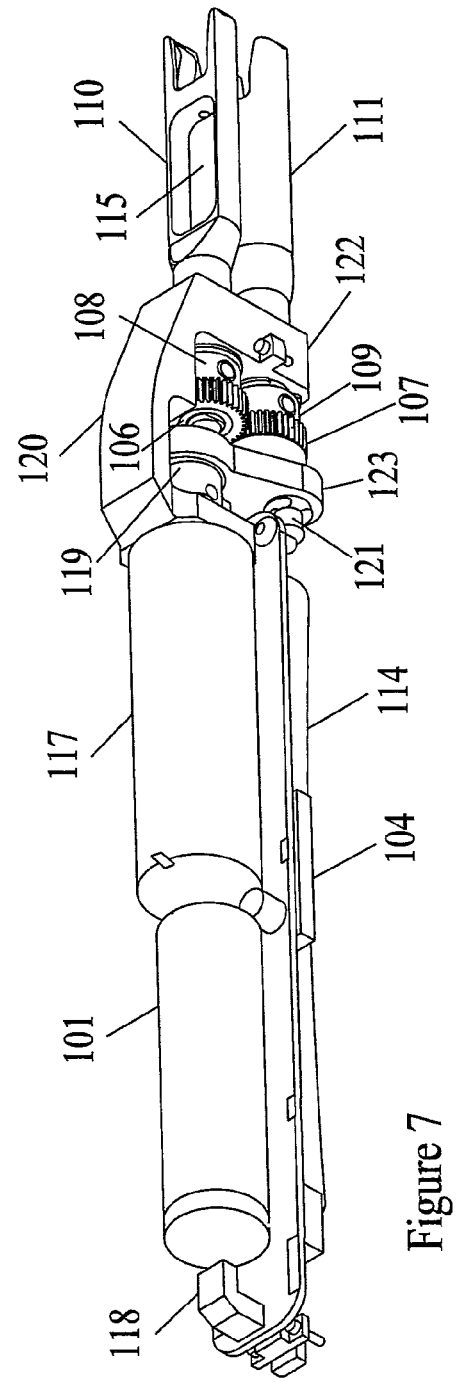
FIG. 7 is a perspective view of the frangible opener of FIG. 6 with the outer cover removed.
Figure 8:
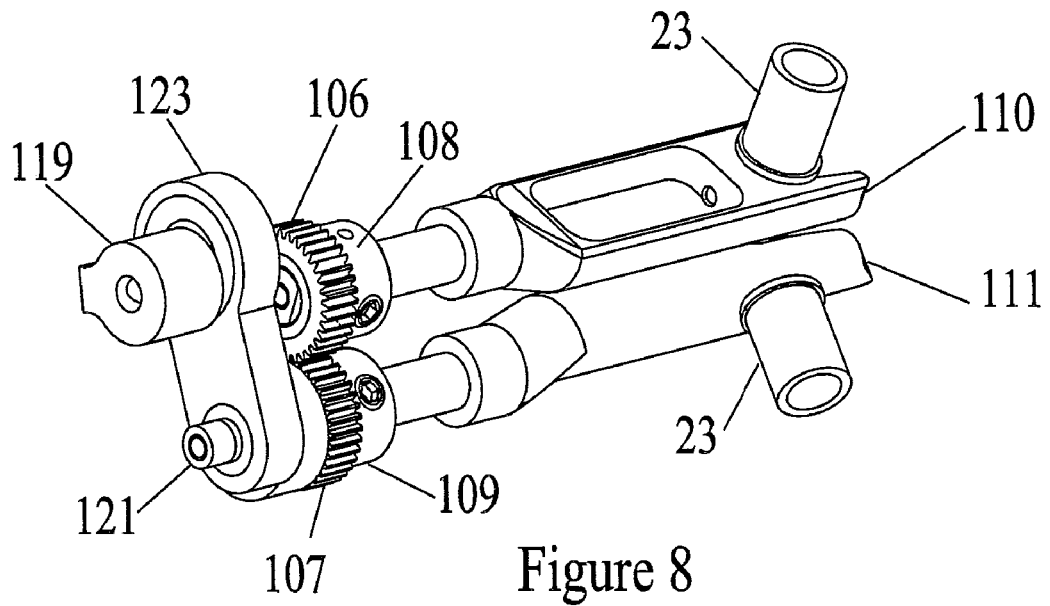
FIG. 8 is a partial perspective view of the gear assembly of the frangible opener of FIGS. 6 and 7.
Figure 9:
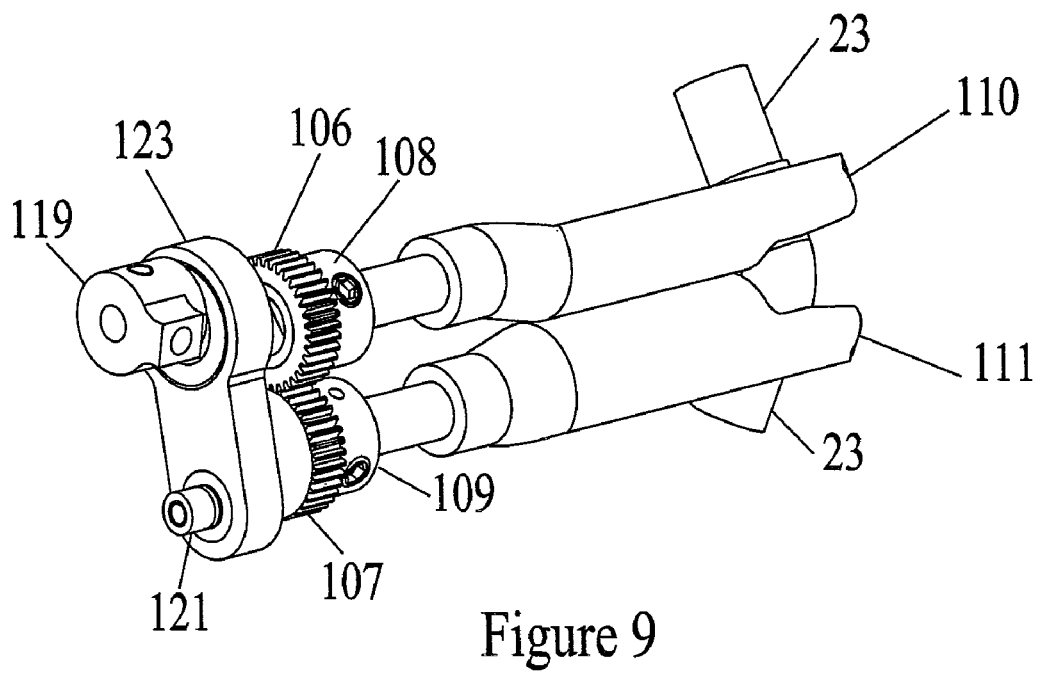
FIG. 9 is partial perspective view similar to FIG. 8 but shows gear movement in the opposite direction.

FIG. 7 illustrates the opener of FIG. 6 without the outer casing 116. Frame support 114 carries optional batteries 101 along with a optional LED light display 118. The motor is illustrated at 117. Switch 104 can be slidably moved by the operator to connect the motor to the power source for selective operation. Alternatively, the switch may be depressed for example, towards motor 117 to make such a connection. A harness or frame 120 is also provided to support the outer casing 116 and to protect and support the crank and gear arrangement described below. The cross-wise portion 122 of the frame support 120 supports the gear shafts 110 and 111 through a bushing or bearing as described with respect to the embodiment of FIGS. 3 and 4. In this embodiment, motor 117 engages crank 119 for providing rotational movement through linkage 123 and pin 121 to gear wheel 107 and through enlarged shaft portion 109 to gear shaft 111. The engagement between the motor 117 and the crank 119 may be through a gear head.

Follower gear 106 rotates along with gear 107 to impart rotational movement, through enlarged portion 108, to gear shaft 110.

Similar to the embodiment of FIGS. 3 and 4, gear 107 rotates in one direction causing gear 106 to rotate in the opposite direction. This imparts opposite rotational movement to opener shaft 110 as compared to that of opener shaft 111 and causes one arm of gripper ends 112 and 113 to move toward each other while the other arm moves toward each other.

In operation, an operator will slide switch 104 to provide power to motor 117 to bring about rotational movement of crank 119, and gear shaft 107. Rotation of 107 will cause opposite direction rotation of opener shafts 110 and 111. The motor 117 can be reciprocal which will cause reciprocal bending of frangible 23 to break the pin contained therein. Limit switches or sensors sensing the end of the rotation range may be used to trigger the reciprocal rotation or the end of rotation.

As with the embodiment of FIGS. 3 and 4, the frangible opener of FIGS. 6 through 9 can also be operated on electric current. In addition, the batteries, if used, can be replaceable or rechargeable using a recharging holder (not shown).

Figure 10:
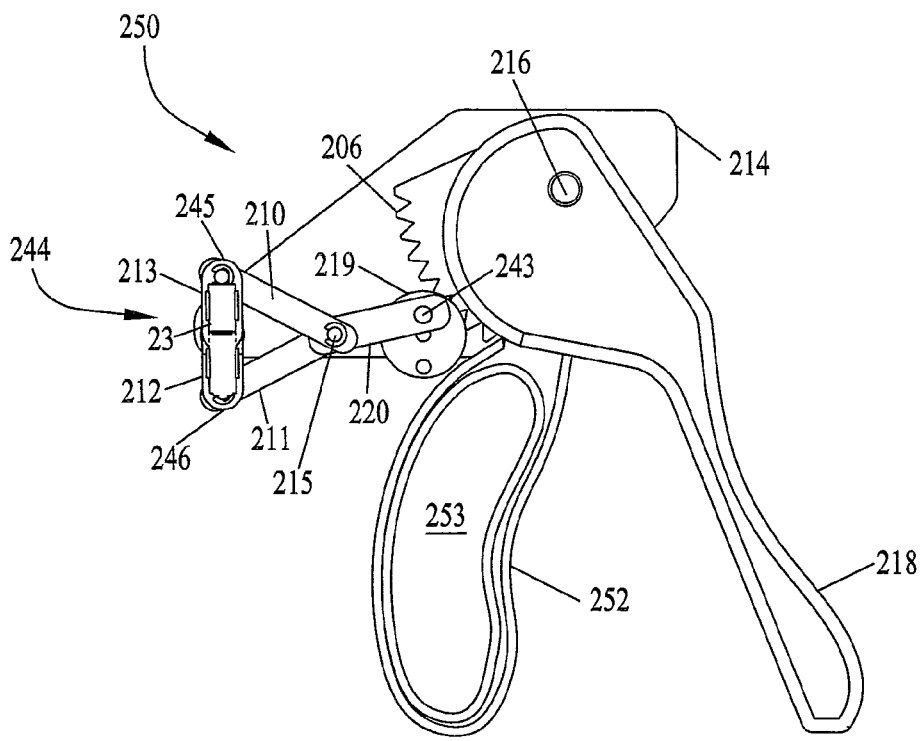
FIG. 10 is a perspective view of an alternative frangible opener.
Figure 11:
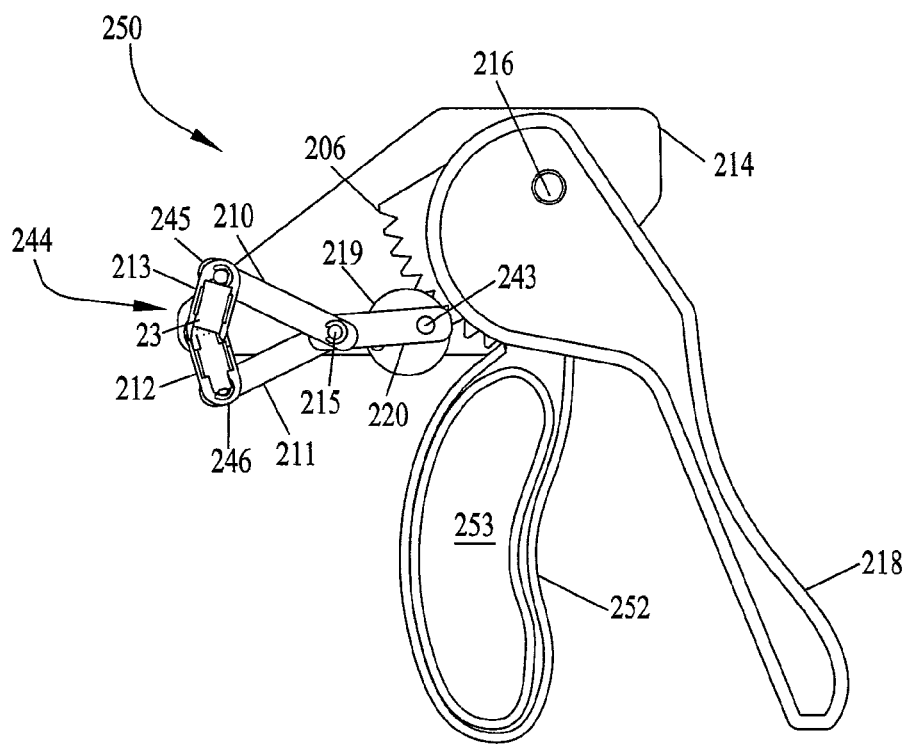
FIG. 11 is a perspective view of the frangible opener of FIG. 10 showing movement in one direction.
Figure 12:
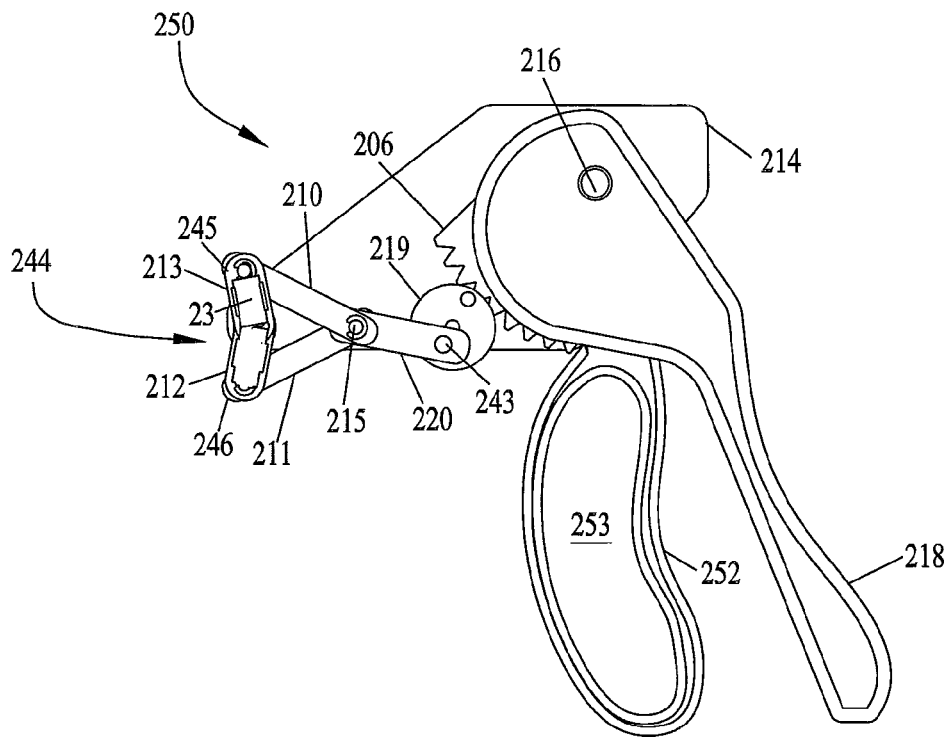
FIG. 12 is a perspective view of the frangible opener of FIG. 11 showing movement in the opposite direction.

FIGS. 10-12 illustrate a manually activated frangible opener that can be operated without motor assistance.

This embodiment includes a base plate 214. Fixed, with respect to the base plate 214 attached to the base through pin 216 is handle 218. A moveable handle 252 having gripper opening 253 is also attached to base plate 214 either through pin 216 or another, not shown, pin.

Movement of handle 252 also brings about movement of driver gear 206, which is attached to a part of the handle 252. Driver gear 206 imparts rotational movement to follow gear 209 (not shown, but see FIG. 13) and through follower gear 209 to crank 219. Crank 219 is connected through pin 243 to connecting link 220. Linkage 210 and 211 are connected through pin 215 to link or linkage 220 and such pin 215 also connects 210, 211 and 220 to base plate 214. Toggle 244 contains an upper toggle portion 245 that is rotatable with respect to the lower toggle portion 246. Upper toggle portion 245 includes a clip 213 for engaging one end of a frangible such as 23. Lower toggle portion 246 also includes a clip 212, for engaging another end of the frangible 23.

Toggle 244 is attached to base plate by a pin (not shown in this embodiment of FIG. 12). This pin permits upper toggle portion 245 to pivot with respect to lower toggle portion 246.

In this embodiment, as with a number of the other embodiments, only the frangible 23 is shown to indicate its breakage. It is understood that the frangible opener can be inside tubing, such as 400.

In operation the tubing containing frangible open 23 is inserted in clips 212 and 213. The frangible open 250 is in the neutral position of FIG. 10. Movement of handle 252 also moves the gear 206, crank 219 and imparts movement of toggle portion 245 with respect to toggle portion 246, through linkage 210, 211 and 220. This is shown in FIG. 11. Further movement of handle 252 results in the movement of toggle portion 245 with respect to 246 shown in FIG. 12.

Figure 13:
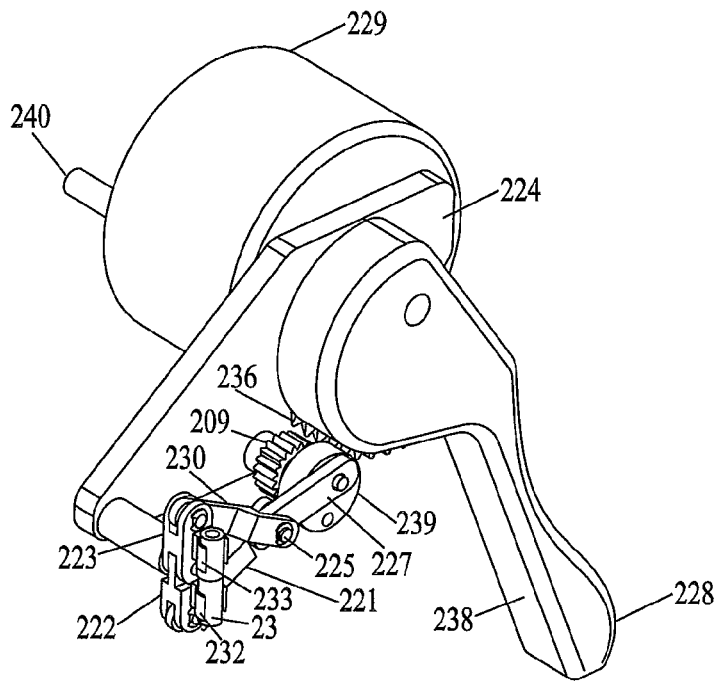
FIG. 13 is a perspective view of a frangible opener similar to FIGS. 10-12 but with a rotary motion device to replace operator hand motion.

FIG. 13 is embodiment similar to FIGS. 10-12, except that rotary element 229 is moved via handle 240 (or an optional motor) to move drive gear 236, follower gear 237, crank 239 and linkages 227, 230 and 221, upper toggle portion 223 (with frangible holding clips 233) and lower toggle portion 222 (with frangible holding clip 232). The frangible opener of this Figure can be held by handle 228 attached to base plate 224.

The operation of the embodiment of FIG. 13 is very similar to that of FIGS. 10-12, except that the initial movement of driver gear 236 is initiated by the rotating element 229. A limit switch or sensor may optionally be provided with this embodiment to trigger reciprocal motion or end of motion.

Figure 14:
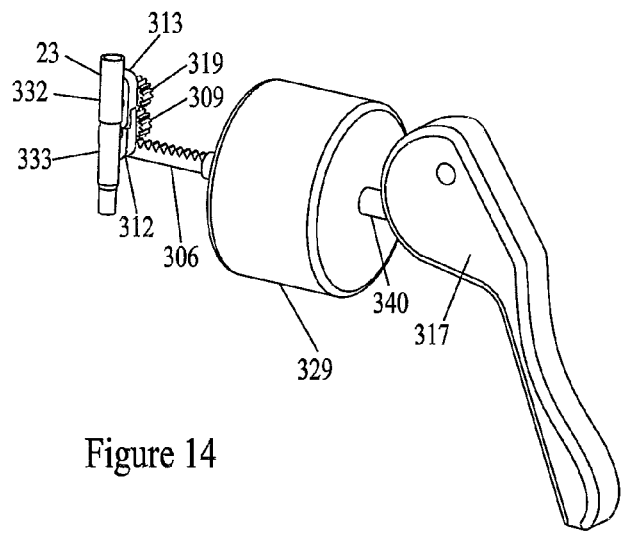
FIG. 14 is a perspective view of an alternative frangible opener using linear motion.
Figure 15:
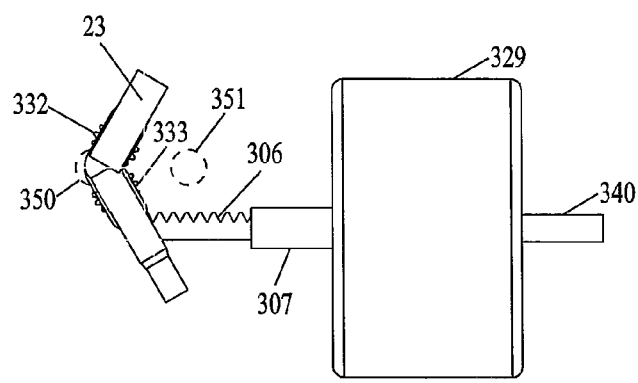
FIG. 15 is a perspective view of the frangible opener of FIG. 14 with movement of the actuator in one direction.
Figure 16:
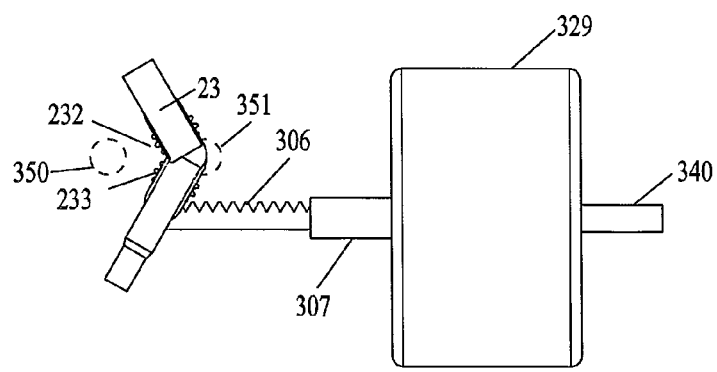
FIG. 16 is a perspective view of the frangible opener of FIG. 15 with movement of the actuator in the opposite direction.

An alternative embodiment is shown in FIGS. 14-16.

In this embodiment handle 317 is connected to linear actuator or linear solenoid through pivot pin 340. Drive rod or linkage 306 is attached to the linear actuator 329 through passage 307. Drive rod cooperates with drive gear 309, which in turn cooperates with follower gear 319. Upper toggle portion 313 having clips 332 for a frangible such as 23 is attached to follower gear 319. Lower toggle portion 312 having frangible clips 333 is attached to drive gear 309.

In operation, movement or rotation of handle 317 imparts rotation to linear actuator 329. Rotation of crank 329 moves drive rod or drive linkage 306 in one direction to rotate drive gear 309. Rotation of drive gear counter clockwise moves toggle follower gear in the opposite direction. This moves upper toggle 313 with respect to 312. Similarly, movement of linkage 306 and drive gear 309 in the opposite direction moves the upper and lower toggle portions 313 and 312 in opposite directions. Reverse or opposite linear motion acting on 306 can be achieved by opposite rotation of crank 329. Although crank 329 is described as being rotated by handle 317, it can also be rotated by through an electrical connection.

Optionally, in an electrical embodiment, sensors or limit switches 350 and 351 may be provided on an outer housing, not shown, to provide a signal to a controller (not shown) to determine when the linear actuator should change direction or stop. The sensors or switches may sense the movement of the toggles 312, 313 as shown or movement of the linear actuator.

The frangible openers of the instant invention, are light in weight for the operator to hold. As the only manual motion may be the push of a switch, the opener also minimizes wrist and hand motion that may result in repetitive strain injury. In a blood processing lab utilizing the centrifuge of FIG. 5 and the bag set of FIG. 1, it is anticipated that single operator may need to open hundreds of frangibles in a single day.

The invention claimed is:

1. A hand held opener for opening a frangible closer comprising
a handle adapted to be gripped by an operator;
a motion actuator;
a first shaft operatively connected to the motion actuator;
a second shaft operatively connected to the motion actuator;
a first gripper portion on an end of the first shaft adapted to grip the frangible closer in a first location, the first gripper portion comprising a first side element and a second side element opposed to the first side element;
a second gripper portion on an end of the second shaft adapted to grip the frangible closer in a second location, the second gripper portion comprising a third side element and a fourth side element opposed to the third side element;
wherein the motion actuator provides first movement that moves the first side element toward the third side element and moves the second side element away from the fourth side element provides movement to the first and second shafts to bend the frangible closer in a first direction, and the motion actuator provides second movement that moves the first side element away from the third side element and moves the second side element toward the fourth side element to bend the frangible closer in a second direction opposite the first direction to open the frangible closer.

2. The hand held opener of claim 1 further comprising
a first gear arrangement connected between the motion actuator and the first shaft;
a second gear arrangement connected between the motion actuator and the second shaft; wherein
the first gear arrangement causes rotation of the first shaft in a first rotational direction; and
wherein the second gear arrangement causes rotation of the second shaft in a second rotational direction opposite the first direction.

3. The hand held opener of claim 2 wherein the first rotational direction is clockwise and the second rotational direction is counter clockwise.

4. The hand held opener of claim 2 wherein the first gear arrangement comprises a first gear and the second gear arrangement comprises a second gear.

5. The hand held opener of claim 1 further comprising a housing; and an electric power system contained in the housing.

6. The hand held opener of claim 1 further comprising an electric power system in the handle.

7. The hand held opener of claim 5 further comprising a bracket attaching the handle to the housing.

8. The hand held opener of claim 7 further comprising a harness attaching the bracket to the housing.

9. The hand held opener of claim 1 further comprising a light to illuminate any frangible opener to be opened.

10. The hand held opener of claim 2 wherein the first gear arrangement also causes rotation of the first shaft in the second rotational direction and the second gear arrangement causes the rotation of the second shaft in the first rotational direction.

11. The hand held opener of claim 3 wherein the first gear arrangement also causes rotation of the first shaft in the second rotational direction and the second gear arrangement causes the rotation of the second shaft in the first rotational direction.

* * * * *